United States Patent [19]

Schneider

[11] 4,153,403
[45] May 8, 1979

[54] MACHINE FOR AUTOMATICALLY MAKING PLASTER SLURRY AND DISPENSING IT TO DENTAL MOLDS

[76] Inventor: Howard S. Schneider, 1871 University Blvd. S., Jacksonville, Fla. 32216

[21] Appl. No.: 852,901

[22] Filed: Nov. 18, 1977

[51] Int. Cl.² ........................... B29B 1/06; B29B 5/06
[52] U.S. Cl. ..................................... 425/159; 425/256
[58] Field of Search ................ 425/155, 157, 159, 256

[56] References Cited

U.S. PATENT DOCUMENTS

| | | | |
|---|---|---|---|
| 3,330,003 | 7/1967 | Eggenberger et al. | 425/159 |
| 3,555,605 | 1/1971 | Angelotti et al. | 425/155 |
| 3,616,495 | 11/1971 | Lemelson | 425/159 X |
| 3,621,519 | 11/1971 | Vandemore et al. | 425/159 X |
| 3,799,719 | 3/1974 | Bonikowski et al. | 425/155 X |
| 4,035,126 | 7/1977 | Manning | 425/157 |

*Primary Examiner*—J. Howard Flint, Jr.
*Attorney, Agent, or Firm*—George H. Mitchell, Jr.

[57] ABSTRACT

Apparatus for automatically mixing dry powder supplied in a quantity determined by a size of a pair of dental molds with liquid to form a slurry, dispensing the slurry to the dental molds and for cleaning the apparatus after the slurry has been dispensed comprises a mixing chamber, a movable dispensing chute to selectively deliver the slurry to the molds and to position the chute over a drain for cleaning, a timer circuit for measuring the amount of liquid supplied to correspond with the amount of the dry powder used, for apportioning the slurry between the two molds and for controlling the supply of liquid for cleaning the apparatus.

27 Claims, 5 Drawing Figures

MACHINE FOR AUTOMATICALLY MAKING PLASTER SLURRY AND DISPENSING IT TO DENTAL MOLDS

This invention relates to dental technology, and more particularly to apparatus for making plaster casts used in the production of artificial dentures.

In U.S. Pat. No. 2,453,914 to Hollenback there is shown a device for mixing a stiff plastic slurry under sub-atmospheric compounds for use in making dental inlays and crowns. No measuring of dry and liquid materials is performed. U.S. Pat. No. 2,805,015 to Miller discloses apparatus for automatically adding dry powder, such as Plaster of Paris or gypsum to a supply of water in a mixing chamber, mixing the materials to form a slurry, discharging the slurry and then admitting a metered amount of water to the chamber to clean it and also to serve as the fluid to be used with a subsequent supply of powder for the next mix. This apparatus has no utility for the preparation of dental molds. U.S. Pat. No. 2,263,797 to Christensen discloses apparatus for use in a foundry for automatically reconditioning the sand used for the molds into which molten metal is poured for casting. U.S. Pat. No. 2,953,359 to Mau discloses apparatus for intermixing solids with solids, or solids with liquids. U.S. Pat. No. 3,297,306 to Napier shows a metering and mixing machine which is self-cleaning during operation. U.S. Pat. No. 3,697,052 to Andris describes an automatic volumetric mixer for combining dry powder with a liquid. Nevertheless, none of the foregoing patents disclose a machine or apparatus capable of automatically performing the operations of the apparatus disclosed herein.

The apparatus disclosed in this application comprises a machine for automatically mixing dry dental plaster powder with a liquid, such as water, dispensing and apportioning the resultant slurry to a pair of molds which are to be used in the preparation of a pair of upper and lower dentures, and finally admitting water, or other cleaning liquid, to apparatus to flush out residues into a drain.

Another object of the invention is to provide a machine having timing means for controlling the quantity of liquid supplied for mixing with a predetermined amount of dry powder for making plaster molds of varying sizes.

A further object is to provide a machine of the above type which can be preset to receive different amounts of dry powder, apportion the correct amount of liquid to be mixed with the powder to form a slurry and to apportion the resultant slurry automatically between two dental molds.

Still another object of the invention is to provide a system which includes prepackaged amounts of a dry powder to be mixed with a liquid to form a slurry for casting dental molds, in which an automatic mixing apparatus can be set to apportion liquid and resulting slurry in accordance with coded indicia supplied by the prepackaged material.

Other objects and advantages will be apparent to those skilled in the art after reading the following specification in connection with the annexed drawings, in which.

Figure 1:
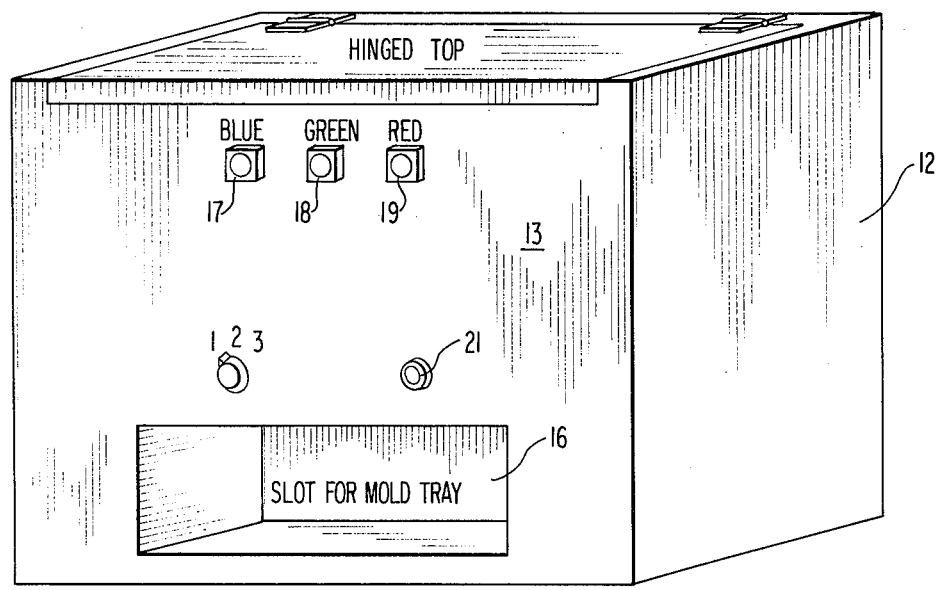
FIG. 1 is a perspective view of the exterior of a preferred form of mixing apparatus constructed in accordance with the present invention.
Figure 2:
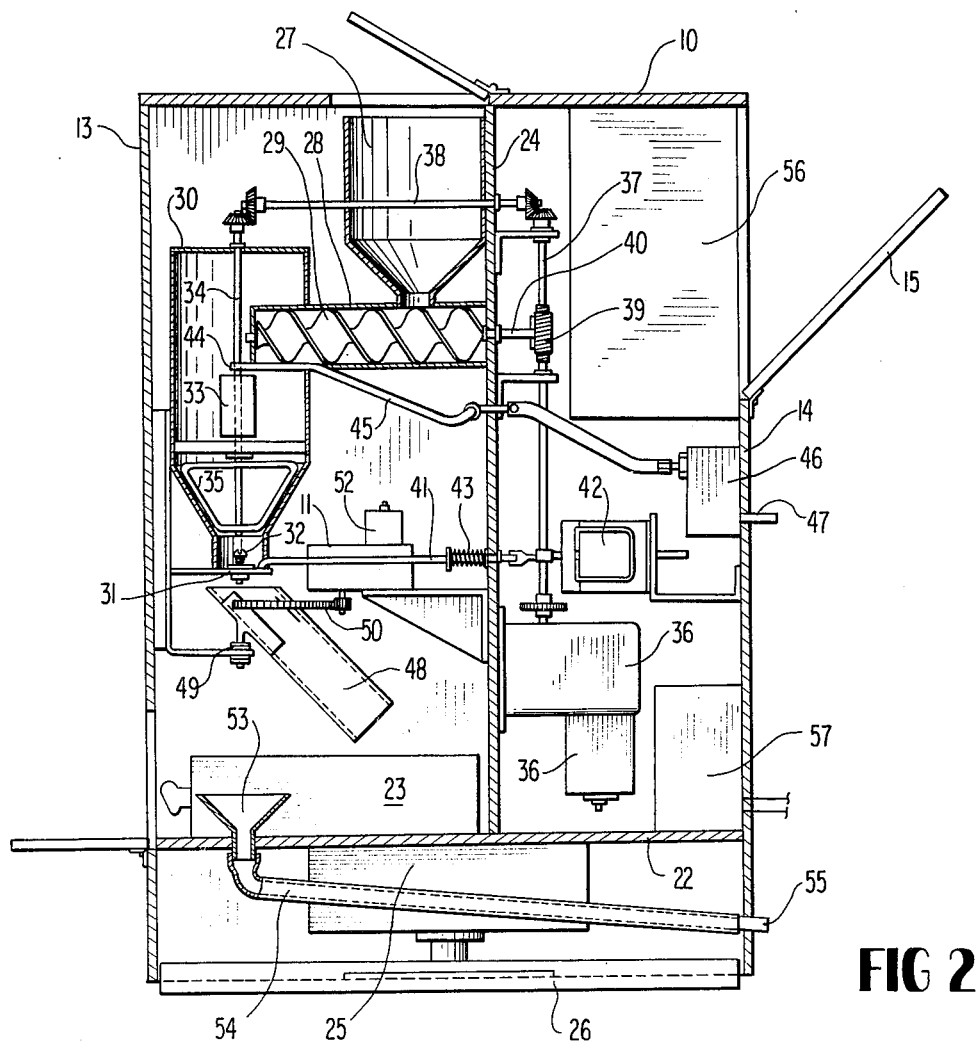
FIG. 2 is a side view, partly in section, of the apparatus of FIG. 1.
Figure 4:
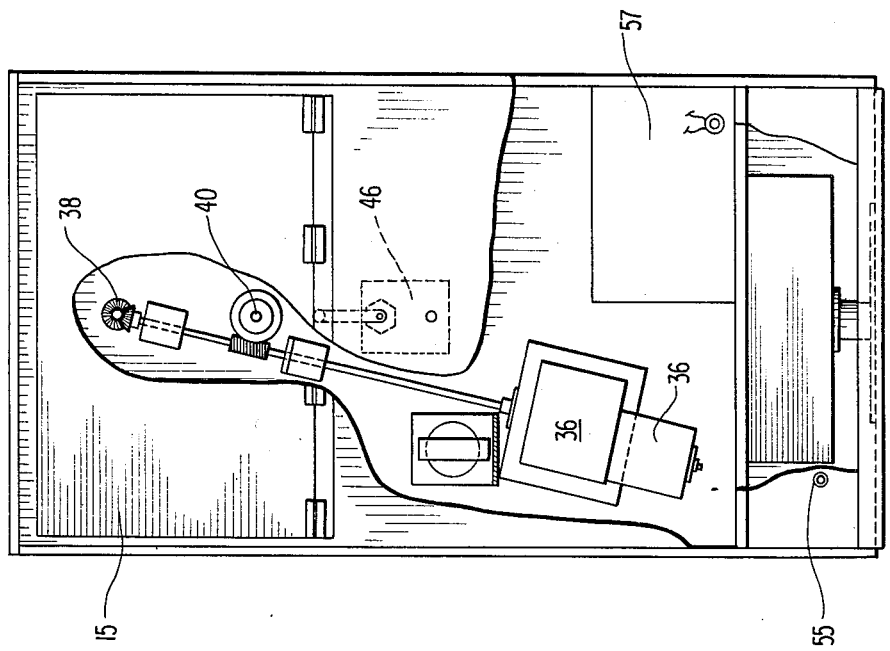
FIG. 4 is a rear view of the apparatus of FIG. 1 with the rear wall removed.

In the drawings, the automatic dental plastic mixing machine is shown as being completely enclosed within a rectangular box provided with a top wall 10 having a hinged cover 11, side walls 12, and front and back walls 13 and 14, the latter provided with a hinged door 15. A slot 16 is provided in the front wall for the insertion of a mold tray and also mounted on the front wall are indicator lights 17, 18 and 19, a three-position switch 20 and a starting push button switch 21.

Within the box there is a floor 22, in alignment with the bottom of the slot 16, which supports a mold tray 23 when inserted through the slot. A vertical wall 24 subdivides the interior into front and back compartments and supports much of the apparatus. The entire enclosure and the apparatus contained therein are supported by an electrically energized vibrator 25 secured to the underside of the floor 2 and mounted on a base 26. In this connection, it can be observed that while the exterior walls of the box extend downwardly to conceal the vibrator and base, they are spaced slightly from the margins of the base and from the support on which the base rests in order to permit the entire apparatus and enclosure to be vibrated by the mechanism 25.

Mounted near the top, and on the front side of interior wall 24, just below the cover 11, is a hopper 27 for dry plaster powder, the outlet of which is connected with the housing 28 of a horizontal screw conveyor 29. The outlet end of the conveyor is connected with the upper portion of a mixing chamber 30 attached to the inside of the front wall 13. The upper portion of the mixing chamber is cylindrical while the lower portion is in the shape of an inverted cone terminating in an outlet provided with a horizontally swingable dump valve 31 mounted on pivot 32. Within the upper portion of chamber 30 there is an upper mixer blade 33 mounted on a vertical rotary shaft 34 which also supports a lower mixer blade 35 disposed angularly at right angles to the upper blade. Shaft 34 and the two mixing blades can be driven by an electrical motor 36, mounted on the back of wall 24, through shafts 37 and 38 by means of appropriate gearing. Shaft 37 also includes a worm gear means 39 which turns the conveyor 29 through the connecting shaft 40.

Dump valve 31 is connected by a horizontal arm 41 to an electrical solenoid 42 which, when energized, rotates the valve to its open position to release the contents of mixing chamber 30. Coil spring 43, surrounding the arm 41, closes the valve 31 when the solenoid is de-energized, and maintains it closed until it is energized again.

In addition to plaster from the hopper 27, water is also added to the chamber 30 to form a slurry when the mixing blades 33 and 35 are rotated. For this purpose, a pair of spray nozzles 44 are positioned in the chamber above the upper blade 33 which are connected to a common supply line 45 which passes through the wall 24 and is connected to an electrically operated valve 46 attached to the inside of the back wall 14 and is provided with an inlet pipe 47 projecting outwardly from the enclosure for connection with the usual water supply in a dentist's office, or wherever the mixing apparatus is to be used.

Figure 3:
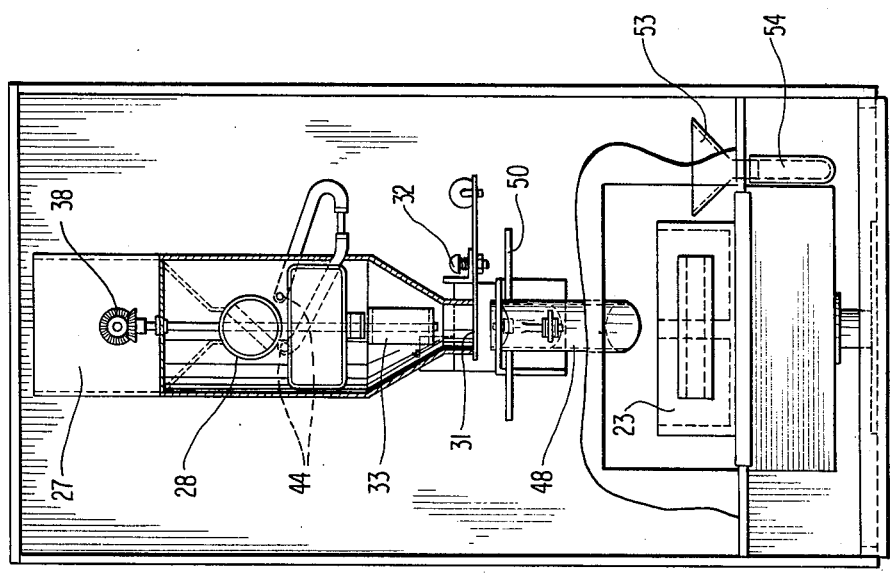
FIG. 3 is a front view, partly in section, of the apparatus of FIG. 1.

The slurry which is discharged when valve 31 is opened drops into the upper end of an inclined tubular chute 48 which is mounted on a bracket 49 for pivotal movement about a vertical axis in such a manner that, while the upper, inlet, end of the chute always remains positioned to receive slurry discharged from valve 31, its lower, discharge, end is movable horizontally between at least three positions. For this purpose, a chute is provided with a sector gear 50 which meshes with a pinion 51, driven through a suitable reversible reduction gearing mechanism 52A by an electric motor 52. Two of these positions are disposed, respectively, over mold No. 1 and mold No. 2 when they are positioned in the mold tray 23, as shown in FIG. 3, while the third position is over a drain funnel 53 mounted in the floor 22 to one side of the mold tray and connected by tube 54 to a drainage outlet fitting 55 projecting outwardly from the back wall 14 for connection with a suitable tube leading to any available drain on the premises.

ELECTRICAL CIRCUIT

Figure 5:
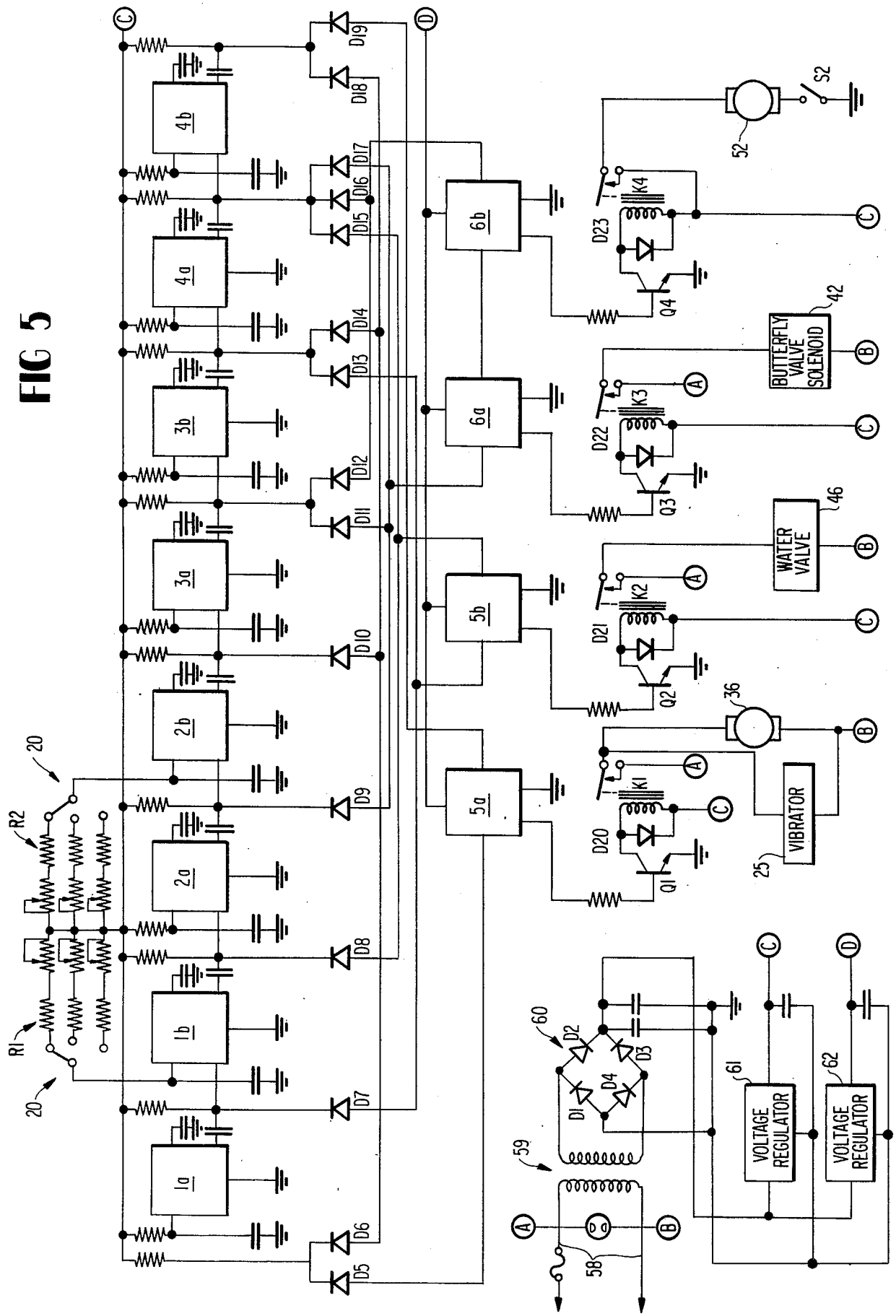
FIG. 5 is a schematic diagram of the electrical circuit for operating the machine.

Operation of various devices is provided by the circuit shown in FIG. 5 comprising a control circuit contained in the enclosure 56 in the back of the cabinet which is reached through access door 15, and a power supply contained in box 57. The power supply consists of a line cord 58 for connection with the usual wall outlet to supply a step-down transformer 59, whose secondary is connected to a full wave rectifier 60 having its negative output grounded and a 16 v positive output connection connected in parallel to two voltage regulators 61 and 62. Taps A and B are also connected from the line cord 58 directly to energize vibrator 25, the mixer motor 36, solenoid valve 46 and dump valve solenoid 42, as will be explained. Regulator 61, for example, is a commercially available IC (integrated circuit) Model MC7812CK which furnishes 12 v DC to output lead C while regulator 62 is an IC Model LM30SK supplying 5 v DC to lead D.

The control circuit comprises eight timer means 1a, 1b, 2a, 2b, 3a, 3b, 4a and 4b, each of which comprises one-half of a commercially available IC (integrated circuit) timing circuit Model SE556V, and four flip-flop circuits 5a, 5b, 6a and 6b, each consisting of one-half of two commercially available ICs Model S7476B. Each of the flip-flop circuits is connected respectively to control the conductivity of a respective transistor Q1, Q2, Q3 and Q4 for energizing respective electromagnetic relays K1, K2, K3 and K4, as will be explained. Transistors Q1 through Q4 may comprise commercially available Model 2N697 while the diodes D5 through D23 may comprise commercially available Model 1N914. The control circuit includes input C for 12 v DC and D for 5 v DC from the power supply outputs C and D. While the circuits and components described above and the operating voltages used comprise a preferred form of suitable power supply and control circuit, it will be understood that they are to be considered as explanatory of one example and not to be considered in a limitative sense.

On the front panel (FIG. 1) there is provided a knob which operates the multi-position two-pole ganged switch 20, which controls timer circuits 1b and 2b for respectively varying the amount of water admitted by valve 46 and the length of time that the dump valve 31 is kept open, together with shifting the position of dump chute 48 when the slurry is apportioned between a pair of dental molds. This is accomplished by the selective insertion of a series of fixed and adjustable resistors, indicated generally by R1 and R2 in FIG. 5, between the voltage supply line C and the inputs of ICs 1b and 2b. In FIG. 1, the three positions of the switch are indicated by numerals, but it will be understood that other indicia, such as geometrical symbols, or variously colored markings, may be used.

In practive it has been found useful to prepackage the dry dental plaster in individual containers, such as bags having various predetermined quantities of plaster corresponding to the sizes of dental molds to be used. In that case the bags are marked such as by means of a different coloring, each color representing an amount of plaster requisite for a particular size mold, that particular mold being also similarly colored. To complete this color coding arrangement the switch positions for switch 20 may also be marked with the appropriate colors to correspond to the timing required for a correspondingly colored bag of prepackaged powder.

OPERATION

Having placed the appropriate sized pair of molds in the tray 23 and inserted the tray through the slot 16 in the front panel onto the floor 22, the user should be careful to select the package of dental plaster containing the amount proper for the size of the molds which have been inserted. The switch 20 should then be set at the correct position, in accordance with the color keyed system described above, or as determined by any other circumstances, and the dry powdered plaster is then emptied from the container into the hopper 27. The operator then pushes the starting push button switch 21, located on the front panel with the result that the following three operations are initiated simultaneously.

1. Flip-flop 5a is set, which makes the transistor Q1 conductive and energizes relay K1 to close the circuit to the leads A and B of the line cord to start the mixer motor 36 and the vibrator 25. This causes the conveyor 29 to begin moving the dry plaster from the hopper into the mixing chamber 30 and rotates the mixer blades 33 and 35. The vibrator 25 is also energized to vibrate the entire unit which assists the gravity flow of the mixture and remove bubbles from the slurry after it is in the molds.

2. Since the dump chute 48 was finally positioned over the drain 53 when power was turned off at the end of a previous operating cycle and has remained in that position to ensure that any remaining residues are discharged only into the drain, the initial operation of push button 21 at the beginning of any succeeding cycle must return the dump chute to its position over one of the molds in the tray. This occurs as a result of the stepping of flip-flop 6b which energizes relay K4 through the conductant of transistor Q4. This closes the circuit from power supply C to motor 52 and a trip (not shown) which has been operated when the chute 48 reached the end of its travel to the position over the drain. This trip reverses the direction of the reduction gearing 52A so that when the circuit is closed at this time the motor is operated to return chute 48 to position 1 over the first mold where another trip (not shown) again reverses the direction of the reduction gearing and the flip-flop is reset to allow motor 52 to be reactivated at the beginning of the next cycle.

3. The timing circuit 1a is started to allow sufficient time for the powder to be moved from the hopper into the mixing chamber 30.

The timing circuit 1a times out when the powder has entered the mixing chamber and it generates a pulse which is a signal to begin the following two simultaneous operations:

1. Flip-flop 5b is set which makes the transistor Q2 conductive to energize relay K2 to energize solenoid 46 to open the water valve.

2. Timing circuit 1b is started to control the exact amount of water supplied by valve 46. Note that in each of the circuits R1 and R2 there is a variable 50K resistor provided for each setting of both poles of switch 20 so that the timing may be adjusted to compensate for the differences in the local water pressures.

When the water valve 46 is opened the water is dispensed from the two nozzles 44 located at each side of and just below the outlet of the conveyor housing 28. These nozzles are aimed so that the water meets at the center just below the outlet of the conveyor housing so that the mixing action is started by the force of the water meeting the powder as it falls from the conveyor. When the proper amount of water has been dispensed, timing circuit 1b times out and its pulse causes the following operations:

1. Flip-flop 5b is reset, making transistor Q2 non-conductive and opening the circuit of relay K2 to de-energize the water valve 46.

2. Timing circuit 2a is started. This circuit provides the necessary time for proper mixing of the powder and water to take place.

As the powder and water fall from the outlet of the conveyor housing the mixing is continued by the rotating action of the upper and lower mixer blades 33 and 35. When the complete mixing has been accomplished, timing circuit 2a times out and its pulse causes the following operations:

1. Flip-flop 6a is set which makes transistor Q3 conductive to energize relay K3 causing the dump valve solenoid 42 to open the dump valve 31 releasing the slurry from the mixing chamber.

2. Timing circuit 2b is started. This timer is set to allow only the proper amount of slurry to be discharged from the mixing chamber to fill the first mold in the tray 23 with the dump chute 48 in its first position. Note also that there is a 50K variable resistor in the circuit R2 for each setting of the switch 20 to allow for slight adjustment of these mixture levels as can be determined by experiment.

When the desired level of the slurry has been reached in the mold number 1, timing circuit 2b times out which causes the following operations to occur:

1. Flip-flop 6a is reset which de-energizes relay K3 and opens the circuit to the dump valve solenoid 42. This causes the spring 43 to close the dump valve 31.

2. Flip-flop 6b is set which makes transistor Q4 conductive, energizing relay K4 to close the circuit for the dump chute motor 52 to begin swinging the dump chute 48 from its position over mold number 1 to a position over mold number 2.

3. Timing circuit 3a is started. This timer is designed to provide sufficient time for the dump chute to move to the next position over mold number 2.

When the dump chute has reached the correct position over mold number 2 it encounters a microswitch S2 which momentarily cuts off the circuit to the dump chute motor 52. When the timing circuit 3a times out the following operations occur:

1. Flip-flop 6b is reset so that the dump chute motor 52 can be re-energized at a later time.

2. Flip-flop 6a is set to re-energize the dump valve 42 through transistor Q3 and relay K3 which opens the dump valve 31 for dispensing slurry to mold number 2 in the tray 23.

3. Timing circuit 3b is started to provide sufficient time for the remaining slurry to be dumped into the second mold.

After completing this second dispensing operation timing circuit 3b times out and the following operations are set in motion:

1. Flip-flop 6a is again reset and the dump valve is closed by spring 43.

2. Flip-flop 6b is set and the dump chute motor 52 is again energized to start moving the chute to its final position over the drain 53.

3. Flip-flop 5b is set, thus reopening the water valve 46.

4. Timing circuit 4a is started. This timing circuit allows for the cleaning part of the operating sequence to take place.

I claim:

1. In apparatus for automatically mixing dry dental plaster and water and filling a dental mold with the resulting slurry, the combination includes:
   a. mixing chamber means including agitating means for accepting a predetermined quantity of dry plaster and liquid and forming a slurry therefrom
   b. means for dispensing a measured amount of said slurry to a dental mold
   c. and means for introducing a liquid to said mixing chamber means and said dispensing means for flushing out residues of said slurry 2. The invention defined in claim 1 which includes means for vibrating said mixing chamber means during the forming of said slurry.

3. The invention defined in claim 1 which includes means for vibrating said dispensing means while dispensing said slurry.

4. The invention defined in claim 1 which includes means for vibrating said molds during said dispensing of slurry.

5. The invention defined in claim 1 wherein said mixing chamber means and dispensing means are mounted on common support means, said support means including electrical vibrator means for vibrating all of said elements while liquid is introduced to flush out residues of slurry.

6. The invention defined in claim 1 wherein said dispensing means also includes means for automatically apportioning said slurry between a pair of dental molds.

7. The invention defined in claim 1 wherein said mixing chamber means (a) includes electric circuit means including motor means for operation of said agitating means and timer means for controlling the duration of said operation.

8. The invention defined in claim 7 wherein said means for introducing a liquid (c) includes circuit means which includes electric valve means for admitting liquid from a liquid supply to said mixing chamber means (a) and means for controlling the amount of said liquid admitted.

9. The invention defined in claim 8 wherein said means for controlling the amount of liquid admitted comprises timer means in said circuit means.

10. The invention defined in claim 1 wherein said dispensing means (b) includes electric circuit means including electric dump valve means to control discharge of slurry from said mixing chamber and timer means to control said dump valve means.

11. The invention defined in claim 10 wherein said dispensing means (b) includes means to discharge slurry to two dental molds and said circuit means includes means to control said dump valve means to apportion slurry to said molds.

12. The invention defined in claim 11 wherein said means to discharge slurry includes electrically operable movable chute means and said circuit means includes means to control the position of the chute means and to control said dump valve means.

13. The invention defined in claim 12 wherein said circuit means includes timer means to control said chute means and dump valve means.

14. The invention defined in claim 1 wherein said dispensing means (b) includes electric circuit means which includes electrically operable chute means movable between a first position to discharge slurry to a first dental mold, a second position to discharge slurry to a second mold and a third position to discharge slurry and cleaning liquid to a drain and means for automatically positioning said chute means.

15. The invention defined in claim 14 wherein said means for introducing liquid (c) includes electrically operable valve means in said circuit means for automatically controlling the introduction of liquid when the chute means is in the third position.

16. The invention defined in claim 15 wherein said means for dispensing slurry (b) includes electrically operated dump valve means and said circuit means includes for automatically controlling the opening of said dump valve means when the chute means is in the third position.

17. The invention defined in claim 16 wherein said circuit means includes timer means for controlling the chute means, the valve means for introducing liquid and the dump valve means.

18. The invention defined in claim 1 wherein said mixing chamber means (a) includes hopper means for receiving a quantity of dry plaster, a chamber for mixing dry plaster with liquid, electrically operated conveying means for moving plaster from the hopper means to the mixing chamber at a controlled rate, electrically operated valve means admitting a predetermined amount of liquid to the chamber, electrically operated mixer means in the chamber, and electrical circuit means for controlling the amount of liquid admitted and the duration of operation of the mixer means.

19. The invention defined in claim 18 wherein said circuit means includes means for varying the amount of liquid admitted and the duration of said mixer operation in proportion of the amount of plaster received in the hopper means.

20. The invention defined in claim 19 wherein said dispensing means (b) includes electrically operable dump valves means controlled by the circuit means to dispense slurry automatically in repsonse to completion of said mixer operation.

21. The invention defined in claim 20 wherein said dispensing means (b) includes electrically operable chute means for dispensing slurry to two dental molds and said circuit means includes means for automatically proportioning slurry to the two molds.

22. The invention defined in claim 21 wherein said means for flushing out residues (c) includes drain means to receive slurry and liquid from the chute means and said circuit means includes means for automatically introducing liquid to flush out residues in response to completion of dispensing of slurry to said dental molds.

23. The invention defined in claim 19 wherein said circuit means includes timer means for controlling the admission of liquid and duration of said mixer operation.

24. The invention defined in claim 20 wherein said circuit means includes timer means for automatically proportioning the slurry.

25. The invention defined in claim 19 wherein said circuit means includes manually operable switch means for varying the amount of liquid and the duration of mixer operation.

26. The invention defined in claim 25 wherein said dry plaster is prepackaged in individual containers provided with indicia representing the amount of plaster contained therein.

27. The invention defined in claim 26 wherein said manually operable switch means is provided with indicia corresponding to the indicia provided for said containers for assistance in operation of the switch means.

* * * * *